(12) United States Patent
Agrawal et al.

(10) Patent No.: US 10,842,981 B2
(45) Date of Patent: *Nov. 24, 2020

(54) HEMOSTASIS VALVES AND METHODS FOR MAKING AND USING HEMOSTASIS VALVES

(71) Applicant: BOSTON SCIENTIFIC LIMITED, Hamilton (BM)

(72) Inventors: Sumit Agrawal, Haryana (IN); Peeyush Tomar, Uttar Pradesh (IN)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 176 days.

This patent is subject to a terminal disclaimer.

(21) Appl. No.: 15/907,983

(22) Filed: Feb. 28, 2018

(65) Prior Publication Data
US 2018/0256875 A1 Sep. 13, 2018

Related U.S. Application Data

(60) Provisional application No. 62/470,634, filed on Mar. 13, 2017.

(51) Int. Cl.
*A61M 39/06* (2006.01)

(52) U.S. Cl.
CPC ........ *A61M 39/0613* (2013.01); *A61M 39/06* (2013.01); *A61M 39/0693* (2013.01);
(Continued)

(58) Field of Classification Search
CPC .......... A61M 2207/00; A61M 39/0613; A61M 2039/062; A61M 2039/0633;
(Continued)

(56) References Cited

U.S. PATENT DOCUMENTS

| | | | |
|---|---|---|---|
| 2,023,267 | A | 12/1935 | De Saint Rapt et al. |
| 4,000,739 | A | 1/1977 | Stevens |

(Continued)

FOREIGN PATENT DOCUMENTS

| | | |
|---|---|---|
| DE | 29701600 U1 | 7/1997 |
| EP | 0567142 A2 | 10/1993 |

(Continued)

OTHER PUBLICATIONS

International Search Report and Written Opinion for Application No. PCT/US2018/020214, 17 pages, dated May 15, 2018.

*Primary Examiner* — Brandy S Lee
(74) *Attorney, Agent, or Firm* — Seager, Tufte & Wickhem LLP.

(57) ABSTRACT

Hemostasis valves and methods for making and using hemostasis valves are disclosed. An example hemostasis valve may include a main body having a distal end region and a proximal end region. A first seal member may be disposed within the proximal end region of the main body. A cartridge may be at least partially disposed within the proximal end region of the main body. The cartridge may include a second seal member. The cartridge may have one or more projections formed thereon. The proximal end region of the main body may have one or more recesses formed therein. The one or more recesses may be designed to engage the one or more projections. A plunger may be coupled to the proximal end region of the main body.

18 Claims, 10 Drawing Sheets

(52) U.S. Cl.
CPC . *A61M 2039/062* (2013.01); *A61M 2039/064* (2013.01); *A61M 2039/0633* (2013.01); *A61M 2039/0686* (2013.01); *A61M 2207/00* (2013.01)

(58) Field of Classification Search
CPC .... A61M 2039/064; A61M 2039/0686; A61M 39/06; A61M 39/0693
See application file for complete search history.

(56) References Cited

U.S. PATENT DOCUMENTS

| | | | |
|---|---|---|---|
| 4,430,081 A | 2/1984 | Timmermans | |
| 4,436,519 A | 3/1984 | O'Neill | |
| 4,610,655 A | 9/1986 | Mueller | |
| 4,615,531 A | 10/1986 | Green | |
| 4,626,245 A | 12/1986 | Weinstein | |
| 4,629,450 A | 12/1986 | Suzuki et al. | |
| 4,655,752 A | 4/1987 | Honkanen et al. | |
| 4,673,393 A | 6/1987 | Suzuki et al. | |
| 4,705,511 A | 11/1987 | Kocak | |
| 4,723,550 A | 2/1988 | Bales et al. | |
| 4,798,594 A | 1/1989 | Hillstead | |
| 4,895,346 A | 1/1990 | Steigerwald | |
| 4,895,565 A | 1/1990 | Hillstead | |
| 4,909,798 A | 3/1990 | Fleischhaker et al. | |
| 4,917,668 A | 4/1990 | Haindl | |
| 4,960,412 A | 10/1990 | Fink | |
| 5,000,745 A | 3/1991 | Guest et al. | |
| 5,041,095 A | 8/1991 | Littrell | |
| 5,114,408 A | 5/1992 | Fleischhaker et al. | |
| 5,125,903 A | 6/1992 | McLaughlin et al. | |
| 5,149,327 A | 9/1992 | Oshiyama | |
| 5,154,701 A | 10/1992 | Cheer et al. | |
| 5,167,637 A | 12/1992 | Okada et al. | |
| 5,176,652 A | 1/1993 | Littrell | |
| 5,207,656 A | 5/1993 | Kranys | |
| 5,269,764 A | 12/1993 | Vetter et al. | |
| 5,395,349 A | 3/1995 | Quiachon et al. | |
| 5,520,655 A | 5/1996 | Davila et al. | |
| 5,643,227 A | 7/1997 | Stevens | |
| 5,779,697 A | 7/1998 | Glowa et al. | |
| 5,858,007 A | 1/1999 | Fagan et al. | |
| 5,935,112 A | 8/1999 | Stevens et al. | |
| 6,024,729 A | 2/2000 | Dehdashtian et al. | |
| 6,149,632 A | 11/2000 | Landuyt | |
| 6,277,100 B1 | 8/2001 | Raulerson et al. | |
| 6,287,280 B1 | 9/2001 | Lampropoulos et al. | |
| 6,551,283 B1 * | 4/2003 | Guo | A61M 39/06 251/149.1 |
| 6,632,200 B2 | 10/2003 | Guo et al. | |
| 7,081,106 B1 | 7/2006 | Guo et al. | |
| 8,002,749 B2 * | 8/2011 | Macatangay | A61M 39/0613 604/164.01 |
| 2001/0021852 A1 | 9/2001 | Becker et al. | |
| 2002/0010425 A1 * | 1/2002 | Guo | A61M 39/06 604/167.04 |
| 2007/0078395 A1 * | 4/2007 | Valaie | A61M 39/0613 604/164.01 |
| 2015/0105752 A1 * | 4/2015 | Gordon | A61M 39/0693 604/533 |

FOREIGN PATENT DOCUMENTS

WO 9813083 A1 4/1998
WO WO2009139981 A2 11/2009

* cited by examiner

HEMOSTASIS VALVES AND METHODS FOR MAKING AND USING HEMOSTASIS VALVES

CROSS REFERENCE TO RELATED APPLICATIONS

This application claims the benefit of U.S. Provisional Patent Application Ser. No. 62/470,634 filed on Mar. 13, 2017, the disclosure of which is incorporated herein by reference.

TECHNICAL FIELD

The present disclosure pertains to medical devices, and methods for manufacturing medical devices. More particularly, the present disclosure pertains to hemostasis valves and methods for making and using hemostasis valves

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example hemostasis valve is disclosed. The hemostasis valve comprises: a main body having a distal end region and a proximal end region; a first seal member disposed within the proximal end region of the main body; a cartridge at least partially disposed within the proximal end region of the main body, the cartridge including a second seal member; wherein the cartridge has one or more projections formed thereon; wherein the proximal end region of the main body has one or more recesses formed therein, the one or more recesses being designed to engage the one or more projections; and a plunger coupled to the proximal end region of the main body.

Alternatively or additionally to any of the embodiments above, the one or more recesses comprise one or more grooves formed along an inner surface of the proximal end region of the main body.

Alternatively or additionally to any of the embodiments above, the one or more recesses comprise one or more slots formed along the proximal end region of the main body.

Alternatively or additionally to any of the embodiments above, engagement of the one or more projections with the one or more recesses is designed to limit rotation of the cartridge relative to the proximal end region of the main body.

Alternatively or additionally to any of the embodiments above, further comprising a ring member disposed along an outer surface of the proximal end region of the main body.

Alternatively or additionally to any of the embodiments above, wherein the proximal end region of the main body includes one or more threads.

Alternatively or additionally to any of the embodiments above, further comprising a nut threadably engaged with the one or more threads.

Alternatively or additionally to any of the embodiments above, the cartridge includes two projections positioned along opposing sides of the cartridge.

Alternatively or additionally to any of the embodiments above, the proximal end region of the main body includes two recesses.

A hemostasis valve is disclosed. The hemostasis valve comprises: a main body having a distal end region, a side port, and a proximal end region; a high pressure seal member disposed within the proximal end region of the main body; a cartridge at least partially disposed within the proximal end region of the main body, the cartridge including a low pressure seal member; wherein the cartridge has one or more projections formed thereon; wherein the proximal end region of the main body has one or more recesses formed therein, the one or more recesses being designed to engage the one or more projections so as to limit rotation of the cartridge relative to the proximal end region of the main body; and a plunger coupled to the proximal end region of the main body.

Alternatively or additionally to any of the embodiments above, the one or more recesses comprise one or more grooves formed along an inner surface of the proximal end region of the main body.

Alternatively or additionally to any of the embodiments above, the one or more recesses comprise one or more slots formed along the proximal end region of the main body.

Alternatively or additionally to any of the embodiments above, the cartridge includes two projections positioned along opposing sides of the cartridge.

Alternatively or additionally to any of the embodiments above, the proximal end region of the main body includes two recesses.

A hemostasis valve is disclosed. The hemostasis valve comprises: a main body having a threaded proximal end region; a nut threadably engaged with the threaded proximal end region; a first seal member disposed within the threaded proximal end region of the main body; a cartridge at least partially disposed within the threaded proximal end region of the main body, the cartridge including a second seal member; wherein the cartridge a pair of opposing projections formed thereon; and wherein the threaded proximal end region of the main body has a pair of opposing recesses formed therein, the recesses being designed to engage the projections so as to limit rotation of the cartridge relative to the threaded proximal end region of the main body.

Alternatively or additionally to any of the embodiments above, the recesses comprise grooves formed along an inner surface of the threaded proximal end region of the main body.

Alternatively or additionally to any of the embodiments above, the recesses comprise slots formed along the threaded proximal end region of the main body.

Alternatively or additionally to any of the embodiments above, further comprising a plunger coupled to the threaded proximal end region of the main body.

Alternatively or additionally to any of the embodiments above, the first seal member comprises a high pressure seal.

Alternatively or additionally to any of the embodiments above, the second seal member comprises a low pressure seal with at least one cut, slit, or slot formed therein.

The above summary of some embodiments is not intended to describe each disclosed embodiment or every implemen-

BRIEF DESCRIPTION OF THE DRAWINGS

The disclosure may be more completely understood in consideration of the following detailed description in connection with the accompanying drawings, in which.

Figure 1:
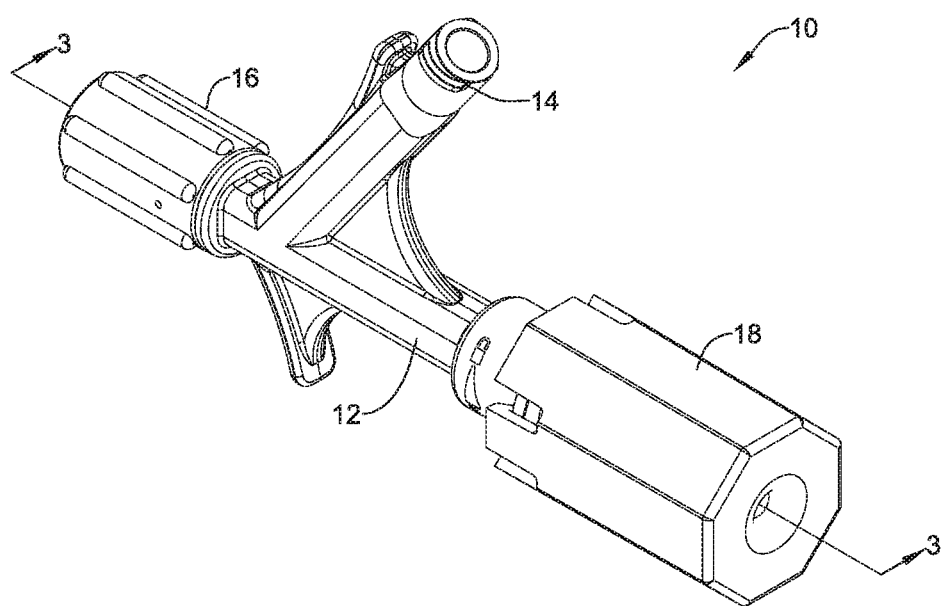
FIG. 1 is a perspective view of an example hemostasis valve.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, for example intravascular procedures, utilize medical devices within body lumens. For example, some intravascular procedures include the placement of a guidewire, guide catheter, interventional device, or the like in a blood vessel. Because fluid under pressure (e.g., blood) is present within the blood vessel, fluid could travel along or through the medical device and escape or leak from the patient. In some instances, it may be desirable to dispose a hemostasis valve or hemostasis valve assembly at the proximal end of a medical device to reduce or otherwise limit the leaking of fluids/blood from the proximal end of the device.

An example hemostasis valve 10 is shown in FIG. 1. The hemostasis valve 10 may include a main body 12. The main body 12 may include a side port 14. The side port 14 may be connected to another device such as an infusion device, an inflation device, or the like. An adapter 16 may be coupled to the distal end of the main body 12. The adapter 16 may be used to couple the hemostasis valve 10 to a device such as a catheter. A plunger 18 may be coupled to the proximal end of the main body 12. The plunger 18 may be used to activate or otherwise close a seal (e.g., as discussed herein) within the hemostasis valve 10. These and other features of the hemostasis valve 10 are discussed herein.

Figure 2:
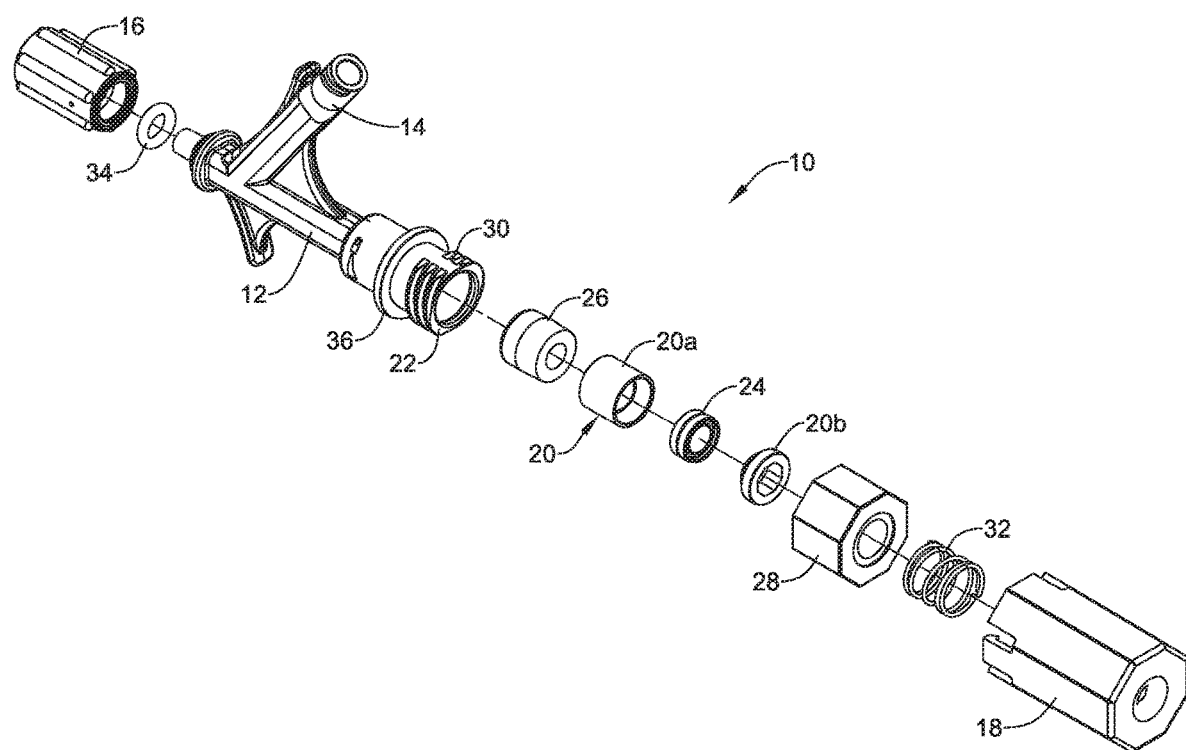
FIG. 2 is an exploded view of an example hemostasis valve.

FIG. 2 is an exploded view of the hemostasis valve 10. Here, the various components of the hemostasis valve 10 can be seen. For example, the hemostasis valve 10 may include a cartridge 20. The cartridge 20, which may include two pieces 20a, 20b that are coupled to one another (e.g., press fit, thermally bonded, adhesively bonded, etc.), may be arranged so that at least a portion thereof can be disposed within a proximal end region 22 of the main body 12. A first seal member 24 may be disposed within the cartridge 20. A second seal member 26 may be disposed within the proximal end region 22 of the main body 12. In at least some instances, the second seal member 26 may be disposed distally of the cartridge 20. The second seal member 26 may include a textured distal surface, grooves or wells formed therein, or the like. In addition or in the alternative, the second seal member 26 may include a proximal region with a reduced diameter. A nut 28 may be coupled to the proximal end region 22 of the main body 12, for example at one or more threads 30 formed along the proximal end region 22.

Other features of the hemostasis valve 10 that can be seen in FIG. 2 include a spring member 32 and an O-ring 34. The spring member 32 may be coupled to the plunger 18. In at least some instances, the spring member 32 may be designed to exert a proximally directed force on the plunger 18. The O-ring 34 may be positioned adjacent to the adapter 16. In addition, a ring member or "snap ring" 36 may be disposed along the proximal end region 22 of the main body 12.

Figure 3:
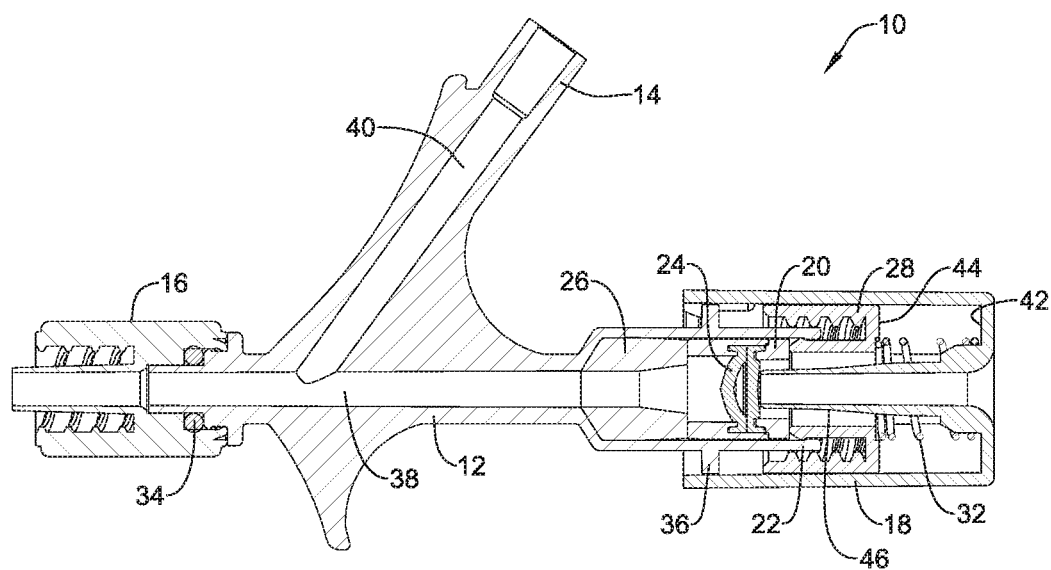
FIG. 3 is a cross-sectional view taken through line 3-3 in FIG. 1.

FIG. 3 is a cross-sectional view the hemostasis valve 10. Here some of the structural features of the hemostasis valve 10 can be seen. For example, the hemostasis valve 10 may include a central lumen 38. In general, the central lumen 38 is designed to be placed into fluid communication with one or more lumens of a device coupled to the adapter 16. A second or infusion lumen 40 may be defined adjacent to the side port 14. The second lumen 40 may be in fluid communication with the central lumen 38.

As indicated above, the hemostasis valve 10 is designed so that it may be coupled to another device. For example, the adapter 16, which may take the form of a Tuohy-Borst or other type of connector, may be engaged with the proximal end of the other device. When connected (and with the plunger 18 in the configuration shown in FIG. 3), the second seal member 26 may be in an open state or configuration. Conversely, the first seal member 24 may be in a closed or sealed configuration when the hemostasis valve 10 is connected to the other device (and with the plunger 18 in the configuration shown in FIG. 3).

Collectively, when the hemostasis valve 10 is connected to another device and in the configuration shown in FIG. 3, the hemostasis valve 10 is able to substantially hold a fluid-tight seal that substantially prevents the backflow and/or leakage of body fluids (e.g., blood). At some point during a medical intervention, it may be desirable to infuse additional fluids such as contrast media through the hemostasis valve 10. This may include attaching an infusion device to the side port 14. Because the first seal member 24 may be designed to substantially prevent the backflow and/or leakage of relatively-low pressure fluids, if the infusion device infuses fluids at a relatively high pressure, it is possible that the infusion fluid may be able to flow through the first seal member 24.

Figure 4:
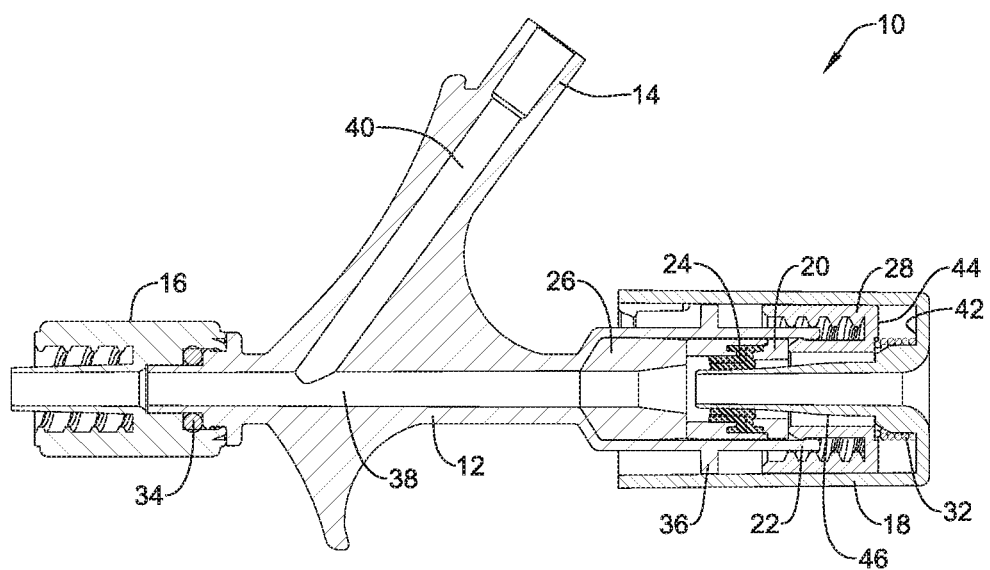
FIG. 4 is a cross-sectional view of an example hemostasis valve.
Figure 5A:
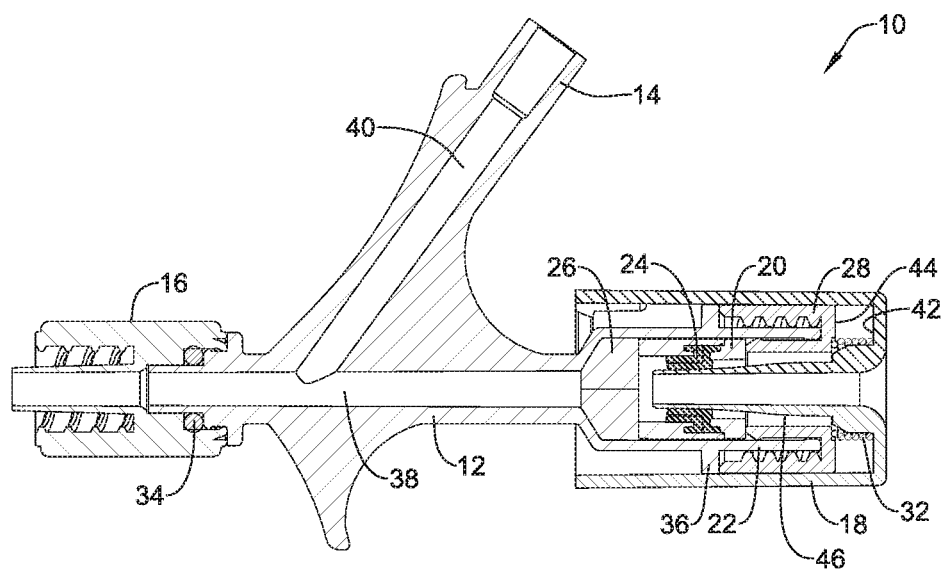
FIGS. 5A-5B is a cross-sectional view of an example hemostasis valve.
Figure 5B:
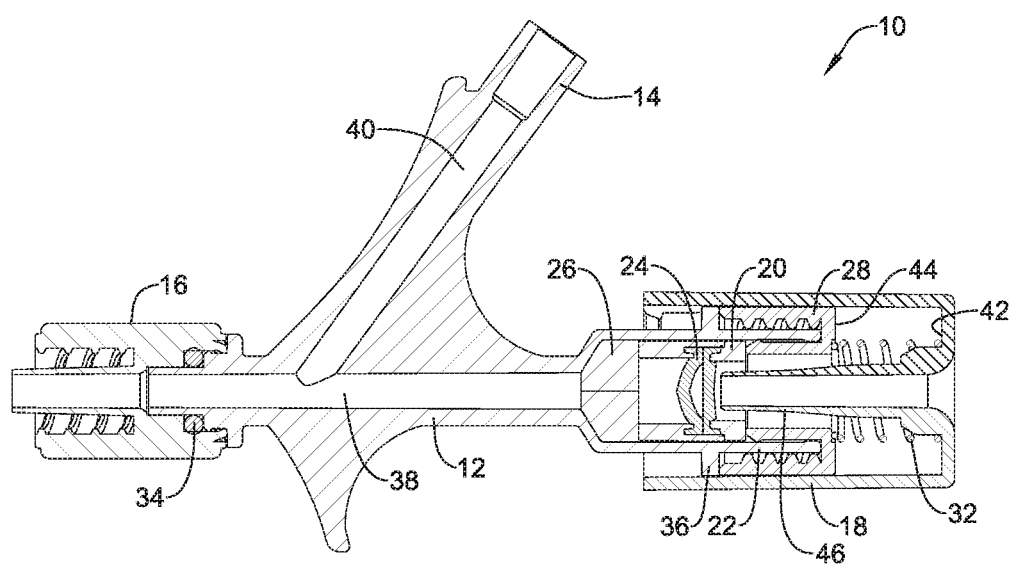

In order to prevent backflow of relatively high pressure fluids, the hemostasis valve 10 can be actuated to close or "seal" the second seal member 26. To do so, the plunger 18 may initially be urged distally until a distally-facing, proximal end surface or cap 42 of the plunger 18 is disposed adjacent to a proximal end region 44 of the nut 28 as shown in FIG. 4. When doing so, a tubular region 46 of the plunger 18 may extend through (and open) the first seal member 24. In addition, a portion of the plunger 18 may move distally beyond the ring member 36. With the cap 42 of the plunger 18 disposed adjacent to the nut 28, the plunger 18 can be rotated (e.g., in a clockwise direction) to close the second seal member 26 as shown in FIG. 5A. This rotation may cause the nut 28 to rotate and move distally. Because the distal end region of the nut 28 may be engaged with the cartridge 20, distal movement of the nut 28 urges the cartridge 20 distally within the proximal end region 22 of the main body 12 such that the cartridge 20 engages and deforms the second seal member 26, thereby shifting the second seal member 26 to the closed or sealed configuration. The plunger 18 may be released or otherwise allowed to move proximally, as shown in FIG. 5B, which may reclose the first seal member 24 (while the second seal member 26 remains closed).

Rotational movement of the nut 28 causes the nut 28 to translate and engage the cartridge 20, which in turn engages and closes the second seal member 26. Typically, the axial movement of the cartridge applies an axial force onto the second seal member 26, which closes or "seals" the second seal member 26. If the rotational movement of the nut 28 causes the cartridge 20 to rotate, this could lead to rotational forces begin applied to the second seal member 26. If this happens, the second seal member 26 could become distorted/twisted in such a manner that the second seal member 26 may not completely close off or seal the main lumen 38. It may be desirable to limit rotational forces being applied to the cartridge 20 and/or the second seal member 26. Disclosed herein are hemostasis valves that are designed to limit such forces.

Figure 6:
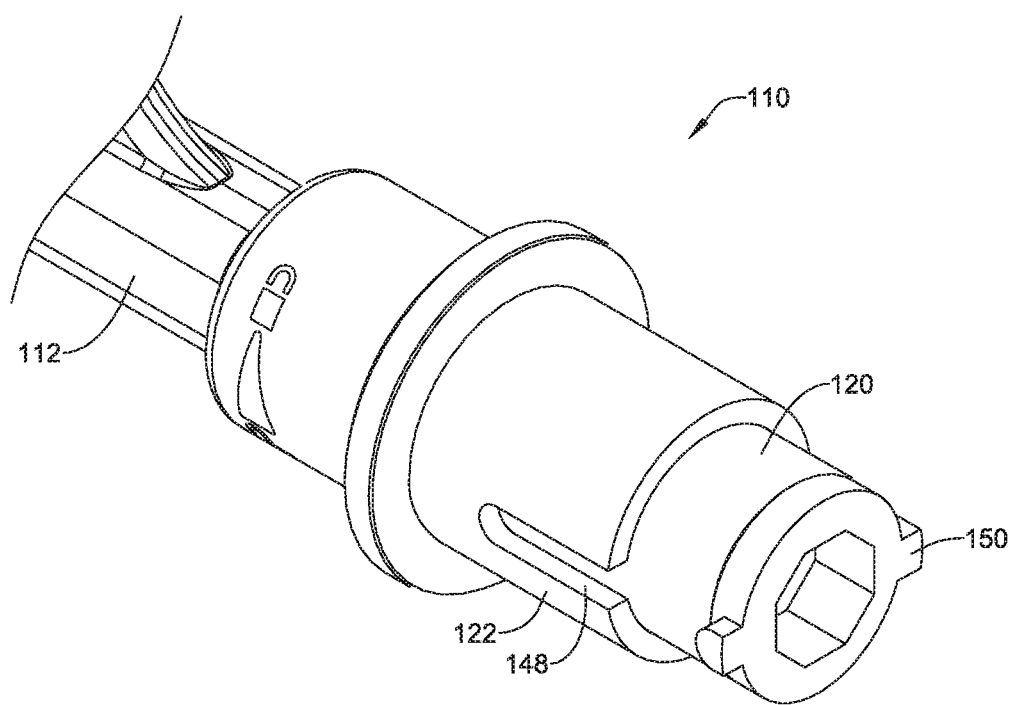
FIG. 6 is a perspective view of a portion of an example hemostasis valve.
Figure 7:
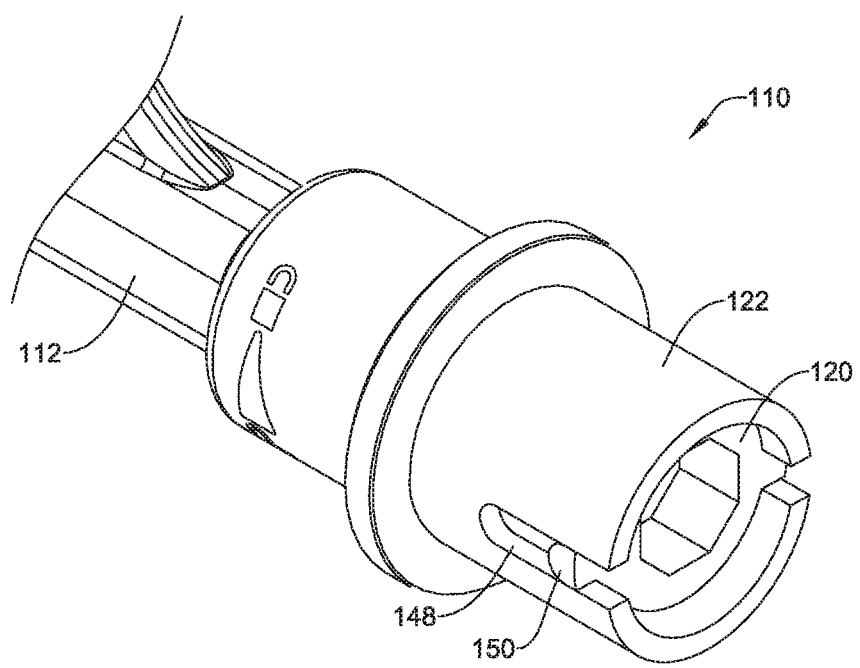
FIG. 7 is a perspective view of a portion of an example hemostasis valve.

FIG. 6 illustrates a portion of an example hemostasis valve 110 that is similar in form and function to other hemostasis valves disclosed herein. While only a portion of the hemostasis valve 110 is shown, it can be appreciated that the reminder of the hemostasis valve 110 may include structures similar to or the same as those in the hemostasis valve 10 described above. In this example, the proximal end region 122 of the main body 112 may include one or more slots or recesses 148. In addition, the cartridge 120 may include one or more wings or projections 150. When the cartridge 120 is disposed within the proximal end region 122 of the main body 112, the wings 150 may fit within the recesses 148. When axial forces are applied to the cartridge 120 (e.g., by the nut 28), the cartridge 120 will begin to translate relative to the main body 112. When doing so, the projections 150 will translate along the recesses 148 as shown in FIG. 7. Because of structural relationship between the projections 150 and the recesses 148, rotation of the cartridge 120 is reduced or otherwise eliminated as the cartridge moves distally within the proximal end region 122.

It can be appreciated that a number of variations are contemplated for the hemostasis valve 110. For example, in some instances, the proximal end region 122 may include a single recess 148, two recesses 148, three recesses 148, four recesses 148, or more. The recesses 148 may be arranged in a number of suitable manners. In some instances, the recesses 148 may be evenly spaced about the proximal end region 122. Alternatively, the recesses 148 may be unevenly spaced. Similarly, the cartridge 120 may include a suitable number of projections 150 such as one, two, three, four, five, six, or more. The projections 150 may be evenly spaced or unevenly spaced about the cartridge 120. In some instances, the number of projections 150 and the number of recesses 148 may be the same. Alternatively, the number of projections 150 may differ from the number of recesses 148.

Figure 8:
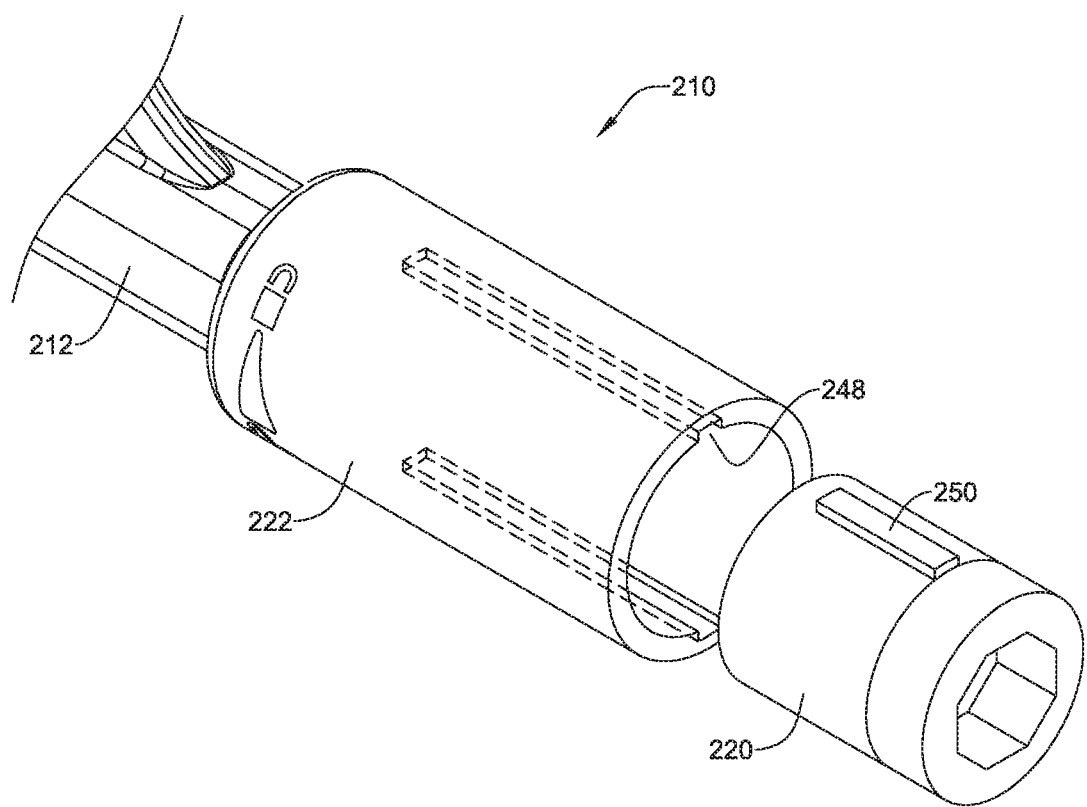
FIG. 8 is a perspective view of a portion of an example hemostasis valve.
Figure 9:
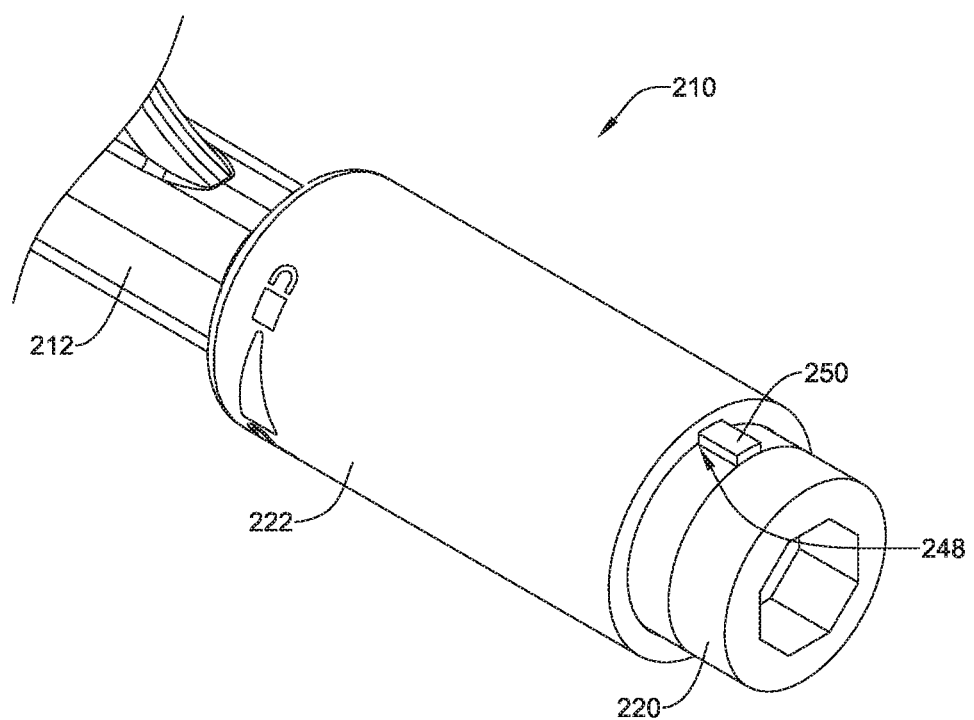
FIG. 9 is a perspective view of a portion of an example hemostasis valve.

FIG. 8 illustrates a portion of an example hemostasis valve 210 that is similar in form and function to other hemostasis valves disclosed herein. In this example, the proximal end region 222 of the main body 212 may include one or more internal grooves 248. In addition, the cartridge 220 may include one or more wings or projections 250. The projections 250 may extend along a portion of the length of the cartridge 220 or a portion of the length. When the cartridge 220 is disposed within the proximal end region 222 of the main body 212, the wings 250 may fit within the grooves 248. Because of this, rotation of the cartridge 220 is reduced or otherwise eliminated as the cartridge moves distally within the proximal end region 222 as shown in FIG. 9.

The materials that can be used for the various components of the hemostasis valve 10 (and/or other hemostasis valves disclosed herein) and the various components thereof disclosed herein may include those commonly associated with medical devices. For simplicity purposes, the following discussion makes reference to the main body 12 and other components of the hemostasis valve 10. However, this is not intended to limit the devices and methods described herein, as the discussion may be applied to other hemostasis valves and/or components thereof disclosed herein.

The main body 12 and/or other components of the hemostasis valve 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:
1. A hemostasis valve, comprising:
   a main body having a distal end region and a proximal end region;
   a cartridge at least partially disposed within the proximal end region of the main body, the cartridge including a first seal member;
   a second seal member disposed within the proximal end region of the main body;
   wherein the cartridge has one or more projections formed thereon;
   wherein the proximal end region of the main body has one or more recesses formed therein, the one or more recesses being designed to engage the one or more projections;
   wherein the proximal end region of the main body includes one or more external threads;
   a nut threadably engaged with the one or more external threads; and
   a plunger coupled to the proximal end region of the main body, adjacent the nut.
2. The hemostasis valve of claim 1, wherein the one or more recesses comprise one or more grooves formed along an inner surface of the proximal end region of the main body.
3. The hemostasis valve of claim 1, wherein the one or more recesses comprise one or more slots formed along the proximal end region of the main body.
4. The hemostasis valve of claim 1, wherein engagement of the one or more projections with the one or more recesses is designed to limit rotation of the cartridge relative to the proximal end region of the main body.
5. The hemostasis valve of claim 1, further comprising a ring member disposed along an outer surface of the proximal end region of the main body.
6. The hemostasis valve of claim 1, wherein the cartridge includes two projections positioned along opposing sides of the cartridge.
7. The hemostasis valve of claim 1, wherein the proximal end region of the main body includes two recesses.
8. A hemostasis valve, comprising:
   a main body having a distal end region, a side port, and a proximal end region;
   a high pressure seal member disposed within the proximal end region of the main body;
   a cartridge at least partially disposed within the proximal end region of the main body, the cartridge including a low pressure seal member;
   wherein the cartridge has one or more projections formed thereon;
   wherein the proximal end region of the main body has one or more recesses formed therein, the one or more recesses being designed to engage the one or more projections so as to limit rotation of the cartridge relative to the proximal end region of the main body;
   wherein the proximal end region of the main body includes one or more external threads;
   a nut threadably engaged with the one or more external threads; and
   a plunger coupled to the proximal end region of the main body, adjacent the nut.
9. The hemostasis valve of claim 8, wherein the one or more recesses comprise one or more grooves formed along an inner surface of the proximal end region of the main body.
10. The hemostasis valve of claim 8, wherein the one or more recesses comprise one or more slots formed along the proximal end region of the main body.
11. The hemostasis valve of claim 8, wherein the cartridge includes two projections positioned along opposing sides of the cartridge.
12. The hemostasis valve of claim 8, wherein the proximal end region of the main body includes two recesses.

13. A hemostasis valve, comprising:
a main body having a threaded proximal end region;
a nut threadably engaged with the threaded proximal end region;
a cartridge at least partially disposed within the threaded proximal end region of the main body, the cartridge including a first seal member;
a second seal member disposed within the threaded proximal end region of the main body;
wherein the cartridge has a pair of opposing projections formed thereon; and
wherein the threaded proximal end region of the main body has a pair of opposing recesses formed therein, the recesses being designed to engage the projections so as to limit rotation of the cartridge relative to the threaded proximal end region of the main body.

14. The hemostasis valve of claim 13, wherein the recesses comprise grooves formed along an inner surface of the threaded proximal end region of the main body.

15. The hemostasis valve of claim 13, wherein the recesses comprise slots formed along the threaded proximal end region of the main body.

16. The hemostasis valve of claim 13, further comprising a plunger coupled to the threaded proximal end region of the main body.

17. The hemostasis valve of claim 13, wherein the second seal member comprises a high pressure seal.

18. The hemostasis valve of claim 13, wherein the first seal member comprises a low pressure seal with at least one cut, slit, or slot formed therein.

\* \* \* \* \*